United States Patent [19]
Kigawa et al.

[11] Patent Number: 5,965,361
[45] Date of Patent: *Oct. 12, 1999

[54] IN-SITU HYBRIDIZATION METHOD USING RECA PROTEIN AND RECA PROTEIN HAVING MARKER OR LIGAND FOR USE IN SAID METHOD

[75] Inventors: Koji Kigawa; Mikayo Yamanaka; Kayo Kihara, all of Osaka; Eli Mukai, Hyogo; Kazuaki Obata, Osaka, all of Japan

[73] Assignee: Daikin Industries, Ltd., Osaka, Japan

[*] Notice: This patent issued on a continued prosecution application filed under 37 CFR 1.53(d), and is subject to the twenty year patent term provisions of 35 U.S.C. 154(a)(2).

[21] Appl. No.: 08/507,423

[22] PCT Filed: Dec. 27, 1994

[86] PCT No.: PCT/JP94/02276

§ 371 Date: Oct. 30, 1995

§ 102(e) Date: Oct. 30, 1995

[87] PCT Pub. No.: WO95/18236

PCT Pub. Date: Jul. 6, 1995

[30] Foreign Application Priority Data

Dec. 28, 1993 [JP] Japan .................................. 5-338528

[51] Int. Cl.⁶ .............................. C12Q 1/68; C12Q 1/08; C07K 14/00; C07H 21/04
[52] U.S. Cl. .............................. 435/6; 435/7.1; 435/40.5; 435/172.3; 435/810; 530/350; 530/387.1; 536/24.3; 536/24.31; 536/24.32; 935/77; 935/78
[58] Field of Search ................................. 530/350, 387.1; 935/77, 78, 76; 435/4, 6, 7.1, 40.5, 172.3, 810; 536/24.3, 24.31, 24.32

[56] References Cited

U.S. PATENT DOCUMENTS

| | | | |
|---|---|---|---|
| 4,683,202 | 7/1987 | Mullis | 435/91.2 |
| 4,724,202 | 2/1988 | Dattagupta et al. | 435/6 |
| 4,888,274 | 12/1989 | Radding et al. | 6/91.2 |
| 5,223,414 | 6/1993 | Zarling et al. | 435/91 |
| 5,506,098 | 4/1996 | Zarling et al. | 435/6 |

FOREIGN PATENT DOCUMENTS

| | | |
|---|---|---|
| 0 322 311 | 12/1988 | European Pat. Off. . |
| 63-109781 | 5/1988 | Japan . |
| WO85/05685 | 12/1985 | WIPO . |
| WO87/01730 | 3/1987 | WIPO . |
| WO91/17267 | 11/1991 | WIPO . |
| 92/08791 | 5/1992 | WIPO . |
| WO 93/05177 | 3/1993 | WIPO . |
| WO94/03639 | 2/1994 | WIPO . |

OTHER PUBLICATIONS

Freitag, N., and McEntee, K., "Affinity Chromatography of RecA Protein and RecA Nucleoprotein Complexes on RecA Protein-Agarose Columns," *J. Biol. Chem.* 263(36):19525–19534 (1988).

Kido, M., et al., "*Escherichia coli* RecA Protein Modified with a Nuclear Location Signal Binds to Chromosomes in Living Mammalian Cells," *Experimental Cell Res.* 198:107–114 (1992).

Griffith, et al., "Intercalating Drugs Markedly Affect the Ability to the *E. coli* RecA Protein to Insert Small Primers into Homologous Duplex DNA," *J. Call Biochem.* 13E:287 (Suppl.) (1989).

Haase, et al., "Amplification and Detection of Lentiviral DNA Inside Cells," *PNAS* 87:4981–4975 (1990).

Koch, et al., "Oligonucleotide–Priming Methods for the Chromosome–Specific Labelling of Alpha Satellite DNA in situ," *Chromosoma* 98:259–265 (1989).

Weier, et al., "Two–Color Hybridization with High Complexity . . . ," *Chromosome* 100:371–376 (1991).

Di Capua, et al., "Characterization of complexes between recA Protein and Duplex DNA by Electron Microscopy," *J. Mol. Biol.* 157: 87–103 (1982).

Fan, Y.–S., et al., "Mapping small DNA sequences by fluorescence in situ hybridization directly on banded metaphase chromosomes," *Proc. Natl. Acad. Sci. USA 87*: 6223–6227 (1990).

Honigberg, S.M. et al., "Ability of RecA protein to promote a search for rare sequences in duplex DNA," *Proc. Natl. Acad. Sci. USA 83*: 9586–9590 (1986).

Infantolino, D., et al., "HBV–DNA by in situ hybridization: A method to improve sensitivity on formalin–fixed, paraffin–embedded liver biopsies," *Liver 9*: 360–366 (1989).

Saiki, R.K., et al., "Enzymatic Amplification of β–Globin Genomic Sequences and Restriction Site Analysis for Diagnosis of Sickle Cell Anemia," *Science 230*: 1350–1354 (1985).

Van Dekken, H., et al., "Three–dimensional analysis of the organization of human chromosomes domains in human and human–hamster hybrid interphase nuclei," *Journal of Cell Science 94*: 299–306 (1989).

Boehringer–Mannheim Catalog (pp. 197–202) 1994.

Sigma Immunochemicals Catalog (pp. 150–157, 220) 1993.

Knight et al., J. Biol. Chemi. 260 (18):10185–91 (abstr.), Aug. 25, 1985.

*Primary Examiner*—Stephanie W. Zitomer
*Attorney, Agent, or Firm*—Gary R. Fabian; Carol A. Stratford; LeeAnn Gorthey

[57] ABSTRACT

A method for detecting the presence of a double-stranded target nucleic acid sequence contained in fixed cells or cell structures is provided. The method includes the steps of forming the fixed cells or cell structures by fixing cells or cell structures so as to allow a nucleic acid probe to enter, and forming a probe/RecA complex in which a single-stranded probe and RecA protein are stably bound to each other. The probe/RecA complex is allowed to react with the double-stranded target nucleic acid sequence to bind thereto under conditions in which the double-stranded target nucleic acid sequence is not denatured, and by detecting the RecA protein included in the probe/RecA complex, the presence of the double-stranded target nucleic acid sequence is detected.

The invention provides a diagnostic method by which the position of a specific gene or its regulatory region in a chromosome and the presence of a nucleic acid sequence derived from virus can be measured or visualized with high sensitivity and with ease.

34 Claims, No Drawings

IN-SITU HYBRIDIZATION METHOD USING RECA PROTEIN AND RECA PROTEIN HAVING MARKER OR LIGAND FOR USE IN SAID METHOD

This application is a 371 filing of PCT/JP94/02276 filed Dec. 27, 1994 which claims priority of Japanese patent application 5/338528 filed Dec. 28, 1993.

DESCRIPTION

1. Technical Field

The present invention relates to an in situ hybridization method utilizing RecA protein useful in the detection of a double-stranded target nucleic acid sequence existing in cells or cell structures, a kit and RecA protein including a label or ligand used to practice the method.

2. Background Art

In situ hybridization is a method for hybridizing a nucleic acid probe directly to a target nucleic acid sequence such as DNA and RNA in a cell. This method is applied to fixed permeabilized cells or cell structures (for example, organelles such as nuclei and mitochondria, and parasites such as bacteria and virus) and biological materials such as a fixed chromosome specimen, with a nucleic acid sequence contained therein utilized as a target. Thus, the presence of the target nucleic acid sequence can be detected in a place where it is present, i.e., in situ, and information about the localization of the target nucleic acid sequence can be obtained. In this manner, this method is applicable to a wide range of areas of biomedical research such as developmental biology, cell biology, genetics (in particular, gene mapping), pathology and gene diagnostics.

In isitu hybridization, a target is generally a double-stranded nucleic acid; typically a specific sequence of pathogen or virus and a specific gene of chromosomal DNA. Conventional in situ hybridization adopts a single-stranded labeled nucleic acid probe, which is added to permeabilized cells and heated to a temperature sufficiently high for denaturing a double-stranded target nucleic acid sequence. The probe and the denatured target nucleic acid sequence are then allowed to be hybridized to each other under suitable conditions. Then, probe which has not been bound to the target nucleic acid sequence is removed, and the labelled probe bound to the target nucleic acid sequence in the cells is detected.

This in situ hybridization is widely applied to areas of chromosomal DNA research such as: mapping of the location of a specific gene sequence, and distance from a known gene sequence on a chromosomal DNA (Fan, Y. S., et al., Proc. Natl. Acad. Sci. USA, 87, 6223, 1990, etc.); study of the distribution of satellite DNA or other repeated sequences on a chromosome (Kenji Sugimoto, et al., Clinical Genetics and Molecular Medicine, 1, 348, 1993, etc.); analysis of chromosomal aberrations (Hopman, A.H.N., et al., Histochemistry, 89, 307, 1988, etc.); analysis of a DNA damage site (Baan, R. A., et al., Prog. Clin. Biol. Res., 340A, 101, 1990, etc.); analysis of a chromosome content with a flow cytometer (Trask, B., et al., Hum. Genet., 78, 251, 1988, etc.); and analysis of gene copy number (Kallioniemi, O. P., et al., Proc. Natl. Acad. Sci. USA., 89, 5321, 1992; Kallioniemi, A., et al., Science, 258, 818, 1992, etc.). Furthermore, the method is utilized in research for localization of viral nucleic acid sequences integrated into a host-cell chromosome (Lawrence, J. B., et al., Proc. Natl. Acad. Sci. USA., 87, 5420, 1990, etc.). It is also applied to study of the location of a chromosome by three-dimensional reconstruction of a sectioned nuclei.

Another general application of the in situ hybridization method is as a diagnostic tool for the detection of the presence of virus in a host cell (Han, K. H., et al., J. Virol. Methods, 37, 89, 1992, etc.). In the case where the number of virus particles contained in an infected cell is very small, viral sequences are previously amplified by in situ polymerase chain reaction (in situ PCR) methods (Hasse, A. T., et al., Proc. Natl. Acad. Sci. USA, 87, 4971, 1990).

The in situ hybridization method described above has a number of limitations. For example, it is necessary to denature a double-stranded target nucleic acid sequence. Denaturation is generally conducted by heat treatment of the target nucleic acid sequence, or a sample including the nucleic acid sequence, in the presence or the absence of a specific drug. This heat treatment frequently causes an undesired change in the nucleic acid in the sample. The change can be a structural change of DNA and a random reassociation between nucleic acids with a repeated sequence interposed therebetween. In addition, denaturation requires increased time and effort.

Additionally, in the case where the copy number of the target nucleic acid sequence is extremely low, a long time is required for hybridization, and the hybridization between the probe and the target nucleic acid sequence is inefficient. The problem can be partly overcome by previously amplifying the target nucleic acid sequence by in situ PCR methods. The in situ PCR method, however, is inconvenient and unsuitable for research analysis of the localization of a chromosomal DNA sequence.

As a method for overcoming the above-mentioned limitations and accurately detecting a target sequence of a small copy number without denaturing the target nucleic acid sequence, another in situ hybridization method using RecA protein has been developed, as described in WO93/05177 by Zarling, D. A., et al. This method utilizes a probe/RecA complex in which a single-stranded nucleic acid probe with a label or ligand having a sequence complementary to a target nucleic acid sequence is stably bound to RecA protein. Under conditions where the target nucleic acid sequence is not allowed to be denatured, the complex is allowed to hybridize to the target nucleic acid sequence, and the probe with a label or ligand bound to the target nucleic acid sequence is detected, thereby detecting the target sequence. In this method, the nucleic acid probe includes a detectable label such as a fluorescent indicator, a chemiluminescent agent, an enzymatic label, a radioactive label or a ligand that can be bound to a specific reporter molecule such as biotin and digoxigenin.

When a probe including a label such as a chemiluminescent agent, an enzymatic label or a ligand such as biotin and digoxigenin is used, the probe bound to RecA protein is allowed to bind to a double-stranded target nucleic acid sequence under conditions where the target nucleic acid sequence is not denatured, and unreacted probe is removed. Then, the target nucleic acid sequence is detected by a secondary reaction including a chemiluminescent process, an enzymatic reaction process or a reaction with a reporter molecule such as labeled avidin, streptavidin or an anti-digoxigenin antibody. When a fluorescent indicator is used, the target nucleic acid sequence is detected by using a detecting device with extremely high sensitivity such as a confocal laser microscope. In the method of Zarling et al., it is impossible to use a probe having neither a label nor a ligand.

In order to prepare a probe having a label or ligand, known methods such as a nick translation method and a random priming method can be used. The number of label or ligand that can be incorporated into the probe by such methods is approximately one per several tens to several hundred bases. Thus, the amount of the label or ligand incorporated into the probe is limited. Therefore, the magnitude of an obtained signal is not necessarily sufficient. As a result, a single-copy gene is scarcely detectable, for example, when the target nucleic acid sequence is detected by using a typical fluorescence microscope, in which the probe is counterstained with propydium iodide or the like. Furthermore, when the hybridization between the probe and the target nucleic acid sequence is disturbed by the label or ligand incorporated into the probe, the detection sensitivity is further decreased. In addition, when multiple different target nucleic acid sequences are to be simultaneously detected, it is necessary to previously bind respectively different types of labels or ligands to probes complementary to their target nucleic acid sequences.

DISCLOSURE OF INVENTION

The present invention overcomes the aforementioned problems, while providing a highly sensitive and simple in situ hybridization method utilizing a probe/RecA complex in which RecA protein is stably bound, by which the presence of a double-stranded target nucleic acid sequence is detected by detecting the RecA protein included in the probe/RecA complex coupled to the double-stranded nucleic acid sequence.

The present inventors have found that RecA protein is stably retained in a probe/RecA complex coupled to a target nucleic acid sequence obtained by the method of Zarling, et al. In the case where the RecA protein is bound to the probe, it is considered that in the detection of a target nucleic acid sequence by using, for example, a ligand that can bind to a specific reporter molecule bound to the probe such as biotin and digoxigenin; the reaction efficiency between the reporter molecule and the ligand is decreased, thereby decreasing the detection sensitivity of general detection means such as a fluorescence microscope. From this point of view, the present inventors made an attempt to remove the RecA protein in the probe/RecA complex coupled to the double-stranded target nucleic acid sequence by using various washing agents such as a proteolytic enzyme and a surfactant. It was, however, impossible to remove the RecA protein from the complex without affecting the target nucleic acid sequence and the complex itself. Therefore, it was decided to find a method for detecting the RecA protein in the complex instead of detecting the probe with the label or ligand contained in the probe/RecA protein.

The present inventors prepared RecA protein having a detectable label such as a fluorescent indicator, a chemiluminescent agent, an enzymatic label and a radioactive label or a ligand that can be bound to a specific reporter molecule such as biotin and digoxigenin. It was found that, even when RecA protein having such a label or ligand is used, a probe/RecA complex coupled to a target double-stranded nucleic acid sequence (i.e., double-stranded target nucleic acid sequence/probe/RecA complex) can be efficiently formed, can be highly sensitive to the presence of the target nucleic acid sequence, and can be simply and highly specifically detected by detecting the RecA protein having the label or ligand contained in the complex.

Furthermore, it was found that the presence of the target nucleic acid sequence can be detected by detecting the RecA protein contained in the probe/RecA protein complex coupled to the target double-stranded nucleic acid sequence (i.e., the double-stranded target nucleic acid sequence/probe/ RecA complex) by allowing the probe/RecA complex coupled to the target double-stranded nucleic acid sequence (i.e., the double-stranded target nucleic acid sequence/probe/ RecA complex) to react with an anti-RecA antibody. Thus, the present invention was accomplished.

The invention relates to a method for detecting the presence of a double-stranded target nucleic acid sequence contained in a fixed cell or cell structure. The method comprises the steps of: obtaining the fixed cell or cell structure by fixing a cell or cell structure so as to allow a nucleic acid probe to enter, the cell or cell structure retaining its components and its nucleic acid structure together with its inherent morphological relationships; forming a probe/ RecA complex in which a single-stranded probe and RecA protein are stably bound to each other, the single-stranded probe having a sequence complementary to the double-stranded target nucleic acid sequence; adding the probe/ RecA complex to the fixed cell or cell structure under conditions in which the probe/RecA complex can come in contact with the double-stranded target nucleic acid; causing a reaction in which the probe/RecA complex and the double-stranded target nucleic acid sequence become coupled to each other under conditions in which the double-stranded target nucleic acid sequence is not denatured; removing part of the probe/RecA complex that has not been coupled to the double-stranded target nucleic acid sequence; and detecting the presence of the double-stranded target nucleic acid sequence by detecting the RecA protein included in the probe/RecA complex coupled to the double-stranded target nucleic acid sequence.

BEST MODE FOR CARRYING OUT THE INVENTION

The term "cell" used herein includes eukaryotic cells of animal cells or plant cells and procaryotic cells of bacteria or the like, and further includes various morphologically and structurally different kinds of cells such as germ cells of sperm or an ovum, and somatic cells among the animal cells. Furthermore, the term includes tissue samples of animals and plants including the foregoing cells.

The term "cell structure" used herein includes bacteria, virus, organelles such as nuclei and mitochondria present in the foregoing cells, chromosomes, and parasites such as virus and bacteria present in samples derived from sources such as blood samples.

A target double-stranded nucleic acid sequence contained in the cells or cell structures is typically chromosomal DNA, viral, a double-stranded nucleic acid sequence of a pathogen or relates to pathogenesis in the foregoing parasites.

The cells or cell structures can be prepared from biological materials such as cultured cells, animal or plant tissues, and biological body fluid.

The fixed cells or cell structures can be obtained by the same method as that used in the conventional in situ hybridization. To be brief, the cells or cell structures are fixed, while retaining the inherent morphological relationship as well as the components and nucleic acid structure thereof; by using an organic solvent, an acid, a crosslinking agent or the like, thereby increasing the permeability of the cells or cell structures to a probe having a sequence complementary to the target sequence. As a typical fixing agent, acetic acid, various kinds of salts, methanol, formalin, paraformaldehyde, glutaraldehyde or the like can be used.

The cells or cell structures are generally treated in the presence or in the absence of one or more drugs so as to remove proteins and/or lipids. Examples of such drugs include one or a combination of acid, alcohol and a surfactant, and examples of the treatment include one or a combination of an enzymatic treatment with protease, lipase or the like, a heat treatment, and a washing treatment. As one of the typical known treatments, the cells or cell structures are washed with methanol:acetic acid once or several times.

In the case where the cells are animal tissues, the animal tissues are first fixed by a conventional fixing method using formalin or glutaraldehyde, and embedded in wax or frozen. Then, the resultant tissues are sliced and can be treated with methanol:acetic acid or the like on a solid support such as a slide glass in order to improve the permeability.

The cell structures can be used to determine the intracellular localization of a target gene sequence and to detect the presence and/or the localization of infectious organisms such as virus, bacteria and parasites in the cells. The cell structures such as nuclei and mitochondria can be concentrated by a general fractionating method such as isopycnic centrifugation, and can be prepared with sufficient purity. Then, the concentrated preparation is fixed, i.e. treated as described above to improve the permeability in a solution or fixed on a solid support such as a slide glass, and then dried for use.

The cell structures such as nuclei can be prepared by pretreating cells with a 75 mM KCl solution and removing cytoplasm through a treatment with methanol:acetic acid. Specifically, the cells are collected by centrifugation at a low speed, and suspended in the 75 mM KCl solution. The resultant solution is allowed to stand for 5 to 20 minutes until the nuclei are appropriately swollen, ice cooled methanol:acetic acid is added thereto and the resultant solution is subjected to centrifugation. The procedure of adding ice cooled methanol:acetic acid and centrifuging the solution with gently stirring is repeated, thereby removing the cytoplasm from the nuclei. The thus isolated nuclei can be resuspended in methanol:acetic acid, and approximately 10 µl of the resultant solution can be dropped on a solid support such as a slide glass to be dried and adhered. The fixed nuclei can be stored at a temperature ranging between room temperature and −80° C. Alternatively, the cells collected as above can be washed with a phosphatebuffered saline (PBS), and then fixed through a treatment with 100% methanol or 70% ethanol. The thus fixed cells can be stored at a temperature of −20° C. The stored fixed cells are suspended in a solution, and can be used in a hybridization reaction.

The cell structures such as chromosomes can be obtained from, for example, metaphase cells of lymphocytes in a general method described by Trask, B. J., et al., in Methods in Cell Biology, 35, 16, 1991. The chromosomes are generally treated with methanol:acetic acid and then dropped on a slide glass or the like to be dried and adhered.

The cell structures such as mitochondria and viral particles isolated from cells or blood samples also can be similarly fixed by a general method.

The nucleic acid probe used in the present method is a single-stranded nucleic acid, and typically a single-stranded DNA. The probe can be prepared by denaturing a double-stranded probe complementary to one or both of the strand (s) of the target nucleic acid sequence. Various types of single- or double-stranded probes, including commercially available satellite DNA sequences, can be used in the present method. Alternatively, the probe can be directly prepared from; for example, virus, a plasmid, a cosmid having a specific sequence, or other vectors by a probe preparation method generally known in the art. If necessary, the probe can be prepared by excising a probe DNA moiety from a vector with a restriction enzyme, and isolating a specific restriction enzyme fragment by electrophoresis. The thus obtained probe is generally double-stranded, and can be subcloned to a single-stranded vector such as an M13 phage vector, if necessary. Alternatively, a single-stranded probe can be prepared by an oligonucleotide synthesizing method. When a long probe is required to be prepared, sub-fragments of a probe are first synthesized and then ligated to one another.

The nucleic acid probe preferably has a nucleic acid sequence with homology of at least 90% to 95% with the target nucleic acid sequence, so as to definitely cause a sequence-specific hybridization reaction between the target nucleic acid sequence and the probe. The length of the single-stranded probe can generally be approximately 100 to 1,500 bases, but a longer or a shorter polynucleotide probe can be used.

The amount of the nucleic acid probe used in the present invention can be 300 ng or less under a standard condition, and is preferably from 5 to 100 ng.

The nucleic acid probe is not required to have a label or ligand but can include, if necessary, a detectable level of a fluorescent indicator, a chemiluminescent agent, an enzymatic label, a radioactive label, or a ligand that can be bound to a specific reporter molecule such as biotin and digoxigenin. By using the probe having a label or ligand together with RecA protein; an anti-RecA antibody or a secondary antibody that can be bound to an anti-RecA antibody, each of which has a detectable label or ligand, a signal of the label or ligand can be amplified.

The term "RecA protein" used herein means a group of RecA-like recombinase proteins that are substantially equal to *E.coli* RecA protein and have all of or almost all the functions of *E.coli* RecA protein. Examples of the RecA protein include *E.coli* RecA protein (Shibata, T., et al., Methods in Enzymology, 100, 197, 1983), uvsX protein derived from T4 phage similar to *E.coli* RecA protein (Yonesaki, T., et al., Eur. J. Biochem., 148, 127, 1985), Rec protein derived from *Bacillus subtilis* (Lovett, C. M., et al., J. Biol. Chem., 260, 3305, 1985), Rec1 protein derived from Ustilago (Kmiec, E. B., et al., Cell, 29, 367, 1982), RecA-like protein derived from yeast, a mouse or a human (Shinohara, A., et al., Nature Genetics, 4, 239, 1993), and heat resistant RecA-like protein derived from thermophilic bacteria such as *Thermus aquaticus* (Angov, E., et al., J. Bacteriol., 176, 1405, 1994) or *Thermus thermophilus* (Kato, R., et al., J. Biochem., 114, 926, 1993). Among these proteins, the best characterized RecA protein is from *E.coli*. As the RecA protein derived from *E.coli*, not only the wild type but also a large number of its variant types (such as RecA803: Madiraju, M., et al., Proc. Natl. Acad. Sci. USA., 85, 6592, 1988 and RecA441: Kawashima, H., et al., Mol. Gen. Genet., 193, 288, 1984) can be used.

The RecA protein to be used can be purified from *E.coli* by a general method (for example, Shibata, T., et al., Methods in Enzymology, 100, 197, 1983). Alternatively, commercially available RecA protein (for example, manufactured by Pharmacia) can be used.

The RecA protein can include a detectable label or ligand such as a fluorescent indicator, a chemiluminescent agent, an enzymatic label, a radioactive label, biotin or digoxigenin. Examples of the fluorescent indicator include fluorescein isothiocyanate, carboxymethylindocyanine succinimidyl ester (Cy3™, Cy5™, etc.), rhodamine, Texas red (sulforhodamine), tetramethylrhodamine isothiocyanate, and 7-amino-4-methylcoumarin-3-acetic acid. Examples of the enzymatic label include alkaline phosphatase, peroxidase, and β-galactosidase.

The RecA protein having the label or ligand can be prepared in accordance with a method for binding a label or ligand to protein such as an antibody. For example, the fluorescent indicator (fluorescent pigment) such as fluorescein isothiocyanate (FITC) and tetramethylrhodamine isothiocyanate (TRITC) can be bound to the RecA protein in accordance with a method of Matsuhashi, et al., Seibutsukagaku Jikkenho 15, "Menekigaku Jikken Nyumon", p. 137 (published by Gakkai Shuppan Center). Alternatively, the fluorescent indicator such as carboxymethylindocyanine succinimidyl esters such as Cy3™ and Cy5™ can be bound to the RecA protein in accordance with a method of, for example, Southwick, et al., (Southwick, P. L., et al., Cytometry, 11, 418, 1990). Alternatively, the fluorescent indicator can be bound by using commercially available kits such as FluoroLink-Ab™ Cy3™ Labeling Kit and FluoroLink-Ab™Cy5™ Labeling Kit (manufactured by BIOLOGICAL DETECTION SYSTEMS, INC.). The amount of the fluorescent indicator to be bound to the RecA protein is 1 to 10 molecules, preferably 1 to 6 molecules, per RecA protein monomer.

The chemiluminescent agent such as acridinium ester can be bound to the RecA protein in accordance with a method of, for example, Simpson, J. S. A., et al. (Simpson, J. S. A., et al., Bioluminescence and Chemiluminescence. Basic Chemistry and Analytical Applications. New York: Academic Press 1981, p. 673).

The enzymatic label such as alkaline phosphatase, peroxidase and β-galactosidase can be bound to the RecA protein in accordance with a method of, for example, Matsuhashi, et al., Seibutsukagaku Jikkenho 15 "Menekigaku Jikken Nyumon", p. 151 (published by Gakkai Shuppan Center). The amount of the enzymatic label to be bound to the RecA protein is 1 to 3 molecules, preferably 1 to 2 molecules, per RecA protein monomer.

The radioactive label such as $^{125}$I and $^{131}$I can be bound to the RecA protein in accordance with the method of Matsuhashi, et al., Seibutukagaku Jikkenho 15 "Menekigaku Jikken Nyumon", p. 143 (published by Gakkai Shuppan Center). Alternatively, radioactively labeled RecA protein can be prepared by purifying protein from E.coli cultured in the presence of an amino acid having any of various radioactive labels.

Biotinylated RecA protein can be prepared in accordance with a method of, for example, Seikagaku Jikkenho 11, "Enzyme Immunoassay", p. 24 (published by Tokyo Kagaku Dojin). The amount of biotin to be bound to the RecA protein is 1 to 10 molecules, preferably 1 to 6 molecules, per RecA protein monomer.

Digoxigenine labeled RecA protein can be prepared by a general method (using a kit manufactured by Boehringer Mannheim) from digoxigenin-3-0-succinyl-ε-aminocaproic acid-N-hydroxy-succiimide ester (DiG-NHS) or the like. The amount of digoxigenin to be bound to the RecA protein is 1 to 10 molecules, more preferably 1 to 6 molecules, per RecA protein monomer.

The RecA protein having a label or ligand can be used as a mixture with ordinary RecA protein having neither label nor ligand.

The process for forming the probe/RecA complex is performed in accordance with the description of WO93/05177 and WO93/05178 by Zarling, et al. This process is performed preferably in the presence of a cofactor such as ATPγS, GTPγS, rATP, rATP in an rATP reproduction system (manufactured by Boehringer Mannheim), dATP, a mixture of ATPγS and rATP, a mixture of ATPγS and ADP, a mixture of GTPγS and ADP and a mixture of GTPγS and GDP. A preferred cofactor is ATPγS, rATP or GTPγS. Such a cofactor can be used at a concentration ranging from approximately 0.12 to 12.0 mM, preferably from 0.24 to 7.0 mM.

A probe to be used for preparing the probe/RecA complex can be either single-stranded or double-stranded. Typically, the probe is thermally denatured for 5 minutes at a temperature ranging from approximately 95° C. to 100° C., cooled with ice for approximately 20 seconds to one minute, and then used for the binding reaction with the RecA protein. If necessary, the probe can be centrifuged for approximately 20 seconds at a temperature ranging from 0° C. to 4° C. prior to the binding reaction with RecA protein. The denatured probe can be stored in a freezer at a temperature of −20° C., but preferably it is immediately mixed with a standard RecA reaction solution (Ferrin, L. J., et al., Science, 254, 1494, 1991, Sena, E. P., et al., Nature Genetics, 3, 365, 1993, etc.) including any of the foregoing cofactors and with the RecA protein in a iced water bath. The obtained mixture is allowed to stand at a temperature of 37° C. for 10 to 15 minutes, thereby stably binding the RecA protein to the single-stranded probe. Through this reaction, one molecule of the RecA protein is bound to approximately three bases of the single-stranded probe, resulting in coating the single-stranded probe with the RecA protein.

The concentration of the RecA protein to be reacted with the probe can be changed depending upon the size and amount of the probe, and is preferably approximately 0.5 to 100 μM. The mixing ratio between the RecA protein (monomer) and the bases in the probe is approximately 5:1 to 1:3, preferably 3:1 to 1:2.5. The reaction for forming the probe/RecA complex can be performed in the presence of another protein such as single-strand binding protein (SSB) and bacteriophage T4 gene 32 protein, if necessary, thereby accelerating the reaction.

In order to eliminate the effect of free RecA protein that has not been bound to the probe, carrier DNA or RNA such as salmon sperm DNA and tRNA derived from yeast or E.coli can be added to the mixture after the formation of the probe/RecA complex. Thus, the free RecA protein that has not been bound to the probe is bound to the carrier, thereby preventing the RecA protein from non-specifically binding to nucleic acids or the like other than the target nucleic acid sequence contained in the fixed cells or cell structures. This treatment is useful for decreasing noise signals occurring in the background during observation with a fluorescence microscope or the like. Alternatively, the free RecA protein can be removed by separating the free RecA protein from the probe/RecA complex by general column chromatography. When the probe/RecA complex is prepared by using RecA protein having a detectable label or ligand, post-treatment with the carrier DNA or RNA is effective.

Furthermore, it is possible to omit this procedure by adjusting the ratio between the probe and the RecA protein to be used for preparing the probe/RecA complex.

Alternatively, the probe/RecA protein having a detectable label or ligand can be prepared by stably binding RecA protein having neither a label nor a ligand to a single-stranded probe, and then binding a detectable label or ligand to the RecA protein in the probe/RecA complex by any of the foregoing methods.

The procedure for adding the probe/RecA complex to the fixed cells or cell structures under the conditions where the complex can come in contact with the double-stranded target nucleic acid sequence, and the procedure for binding the probe/RecA complex to the double-stranded target nucleic acid sequence can be performed in accordance with the description by Zarling, et al. Specifically, under conditions where the target nucleic acid sequence is not denatured, i.e., for example, at a temperature lower than that at which double-stranded DNA is denatured, the probe/RecA complex is added to the cells or cell structures including the target nucleic acid sequence; thereby causing a basesequence specific hybridization reaction to bind the double-stranded target nucleic acid sequence to the probe/RecA complex.

This hybridization reaction is carried out by allowing the mixture to stand at a temperature of 37° C. for approximately 1 to 24 hours, preferably 2 to 18 hours, until the probe/RecA complex is coupled to the target nucleic acid sequence at their homologous sites. If necessary, the hybridization reaction can be performed in the presence of another protein such as single-strand binding protein (SSB), topoisomerase I or topoisomerase II, thereby accelerating the reaction. Part of the probe/RecA complex that has not been coupled to the target nucleic acid sequence can be removed by a known washing method. However, it is undesirable to use a washing solution including, for example, a proteolytic enzyme or a high concentration of a surfactant that can dissolve the RecA protein.

Prior to the hybridization reaction, the fixed cells or cell structures can be subjected to a pre-incubation at a temperature ranging from 4° C. to 60° C. in a 10 mM Tris-acetate buffer (pH 7.5) or a treatment with a proteolytic enzyme such as pepsin or proteinase K before adding the probe/RecA complex thereto. Thus, the reaction efficiency of the hybridization reaction can be improved. Alternatively, the cells or cell structures including the target nucleic acid sequence can be treated with ribonuclease, nickase (for example, DNaseI) or ligase.

Alternatively, the fixed cells or cell structures can be treated, prior to the hybridization reaction, with a pre-blocking solution including at least one selected from the group consisting of casein, skim milk, bovine serum albumin, carrier DNA and carrier RNA, if necessary. These materials to be included in the pre-blocking solution prevent the label or ligand bound to the RecA protein and/or the RecA protein itself from non-specifically binding to the fixed cells or cell structures and/or the solid support. When RecA protein including a fluorescent indicator such as FITC, TRITC and carboxymethyl indocyanine succinimidyl esters such as Cy3™ and Cy5™ is used, ordinary RecA protein having neither a label nor a ligand can be added to the pre-blocking solution. Such a treatment can be typically performed by adding the pre-blocking solution to the fixed cells or cell structures.

The fixed cells or cell structures can be hybridized with the probe/RecA complex in the form of a suspended solution. Specifically, the fixed cells or cell structures are suspended in a hybridization reaction solution including the probe/RecA complex, and the obtained suspended solution is allowed to stand for 1 to 24 hours, preferably 2 to 18 hours, at a temperature of, for example, 37° C. After the reaction, the cells are suspended in a washing solution, thereby removing unreacted part of the probe/RecA complex.

When the cells or cell structures fixed on a solid support such as a slide glass is allowed to react with the probe/RecA complex, a reaction solution including approximately 10 to 20 $\mu$l of the probe/RecA complex is generally added to the cells or cell structures fixed on the slide glass. The resultant reaction solution is covered with a coverslide and put in a sealed container with humidity, and hybridization is conducted, for example, at a temperature of 37° C. for approximately 1 to 24 hours, preferably 2 to 18 hours. After the reaction, the resultant solution is washed several times to remove unreacted part of the probe/RecA complex.

The reaction solution used in the hybridization can be typically prepared so that the final concentration of each component therein be within the following range: 1 to 100 mM Tris-acetate buffer, 2 to 20 mM magnesium acetate, 0 to 100 mM sodium acetate, 0.4 to 1 mM dithiothreitol, 0 to 100 mM EGTA, 0 to 50 mM spermidine, 0 to 10% glycerol, 0.24 to 7.0 mM ATP$\gamma$S, rATP or GTP$\gamma$S, 0.5 to 160 $\mu$M RecA protein (merely RecA protein having a label or ligand, a mixture of RecA protein having a label or ligand and ordinary RecA protein, or merely ordinary RecA protein having neither a label nor a ligand), 5 to 100 ng of the probe per reaction, and 0 to 10 $\mu$g of carrier DNA or RNA per reaction.

The procedure for detecting the presence of the double-stranded target sequence can be performed as follows: For example, when RecA protein having a fluorescent indicator such as FITC, TRITC and carboxymethylindocyanine succinimidyl esters such as Cy3™ and Cy5™ is desired to be detected, a fluorescent signal derived from the RecA protein having such a fluorescent label included in the probe/RecA complex bound to the target double-stranded nucleic acid is detected with a fluorescence microscope, a confocal laser microscope or a flow cytometer (FACS=fluorescence activated cell sorter).

RecA protein having an enzymatic label such as alkaline phosphatase, peroxidase or $\beta$-galactosidase can be detected by a known method such as one described in Japanese Patent Publication No. 4-505556, using a coloring substrate for generating an insoluble pigment such as nitro blue tetrazolium and 5-bromo-4-chloro-3-indolylphosphate, or a chemiluminescent substrate such as AMPPD (manufactured by TROPIX).

RecA protein having a radioactive label can be detected by a know method, for example, by autoradiography described by Michihiro Yoshida, Protein, Nucleic Acid and Enzyme, 38, 558, 1993.

RecA protein having a ligand such as biotin and digoxigenin can be detected by allowing avidin/streptavidin, having a detectable label such as FITC-avidin and an anti-digoxigenin antibody, to bind to the protein.

Alternatively, the double-stranded target nucleic acid sequence can be detected by allowing the probe/RecA complex to react with an anti-RecA antibody with or without a label or ligand. When an anti-RecA antibody having a label or ligand is used, the RecA protein contained in the probe/RecA complex coupled to the target nucleic acid sequence is allowed to react with the anti-RecA antibody with a detectable label or ligand, and unreacted part of the anti-RecA antibody is removed. Then, the anti-RecA antibody with a label or ligand bound to the RecA protein is detected in accordance with any of the detection methods for the label or ligand, thereby detecting the target sequence.

An anti-RecA polyclonal antibody can be easily prepared by a general method such as one described by Matsuhashi, et al., Seibutsukagaku Jikkenho 15 "Menekigaku Jikken Nyumon". Furthermore, an anti-RecA monoclonal antibody can be prepared by, for example, a method of Makino, et al. (Makino, et al., J. Biol. Chem., 260, 15402, 1985). An anti-RecA antibody having a detectable label or ligand can be prepared in the same manner as the preparation method for the RecA protein having a detectable label or ligand.

Alternatively, the double-stranded target nucleic acid sequence can be detected by using an anti-RecA antibody and a secondary antibody that can be bound to an anti-RecA antibody. The secondary antibody can include a detectable label or ligand. As the secondary antibody that can recognize an anti-RecA antibody so as to bind thereto, an anti-mouse IgG antibody can be used when the anti-RecA antibody is derived from a mouse; an anti-rabbit IgG antibody can be used when the anti-RecA antibody is derived from a rabbit; an anti-goat IgG antibody can be used when the anti-RecA antibody is derived from a goat; and in general, a commercially available labeled anti-serum (such as an FITC labeled anti-mouse IgG antibody and an FITC labeled anti-rabbit IgG antibody) can be used. The secondary antibody having a detectable label or ligand that can recognize the anti-RecA antibody so as to bind thereto can be prepared in the same manner as the preparation method for the RecA protein having a detectable label or ligand.

Furthermore, by combining the foregoing detection methods and using a combination of RecA protein having a label or ligand, an anti-RecA antibody having a label or ligand, and a secondary antibody having a label or ligand that can be bound to the anti-RecA antibody; it is possible to amplify a resultant signal to be much stronger than one attained by the conventional method.

In another aspect, the invention provides a kit for practicing the present method including a RecA protein having a detectable label or ligand.

Additionally, the invention provides a kit for practicing the present method including a probe/RecA complex in which a probe and RecA protein having a detectable label or ligand are stably coupled to each other.

The invention also provides a kit for practicing the present method including RecA protein and an anti-RecA antibody having a detectable label or ligand.

The invention further provides a kit for practicing the present method including a probe/RecA complex in which a probe and RecA protein are stably bound to each other and an anti-RecA antibody having a detectable label or ligand.

The kit according to the invention can include the following reagents: (1) a reagent for fixing cells or cell structures comprising a 70% to 100% alcohol solution including, for example, 75 mM KCl, acetic acid and the like; (2) a pre-blocking solution comprising a 10 to 100 mM Tris-acetate buffer (pH 7.5) including, for example, 0 to 0.5% Triton X-100, 0.1 to 10% skim milk, casein, bovine serum albumin, 0 to 5 mg/ml of carrier DNA and/or RNA, and 0 to 10 mg/ml of ordinary RecA protein having neither a label nor a ligand; (3) a cell treatment solution comprising a 10 to 100 mM Tris-acetate buffer (pH 7.5) including, for example, 0 to 15 mM magnesium acetate, 0 to 50 mM sodium acetate, 0 to 1 mM dithiothreitol, 0 to 100 mM EGTA [ethylene glycol-bis(β-aminoethyl ether)N,N,N',N'-tetraacetic acid], and 0 to 50 mM spermidin; (4) a concentrated stock of a reaction solution to be diluted at a time of the usage for preparing a reaction solution with, for example, the following composition: a 10 to 100 mM Tris-acetate buffer (pH 7.5) including 2 to 20 mM magnesium acetate, 0 to 100 mM sodium acetate, 0.4 to 1 mM dithiothreitol, 0 to 100 mM EGTA, 0 to 10% glycerol, 0 to 50 mM spermidin, and 0.24 to 7.0 mM ATPγS or GTPγS; (5) a RecA protein solution at a concentration of, for example, 0.1 to 40 μg/μl, wherein the RecA protein includes or does not include a label or ligand, or is a mixture of RecA protein with a label or ligand and RecA protein without a label or ligand; (6) a probe solution including a single-stranded or double-stranded probe at a concentration of, for example, 5 to 100 ng/μl, wherein examples of the probe include those derived from an α satellite DNA sequence specific to each chromosome, from an oncogene sequence, from an antioncogene sequence and from viral gene sequence; (7) a carrier DNA or RNA solution including, for example, salmon sperm DNA and/or tRNA derived from $E.coli$ or yeast at a concentration of approximately 0.01 to 5 mg/ml; (8) a probe/RecA complex solution having, for example, the following composition: 0.5 to 500 ng/μl of a single-stranded probe, 0.01 to 200 μg/μl of RecA protein having a label or ligand and/or ordinary RecA protein, 2 to 75 mM magnesium acetate, 0 to 1.0 M sodium acetate, 0.4 to 5 mM dithiothreitol, 0 to 1.0 M EGTA, 0 to 500 mM spermidin, 0 to 50% glycerol, 0.01 to 1 M Tris-acetate buffer (pH 7.5) including 0.24 to 70 mM ATPγS or GTPγS, wherein the probe/RecA complex solution includes a probe/RecA complex in which RecA protein with a label or ligand and/or ordinary RecA protein are stably bound to a single-stranded DNA, and is prepared by mixing the solutions (4), (5), (6) and, if necessary, (7); (9) an anti-RecA antibody solution including an anti-RecA antibody having a label or ligand at a concentration of, for example, 10 to 1000 μg/ml; (10) a secondary antibody solution including a secondary antibody that has a label or ligand and can be bound to an anti-RecA antibody at a concentration of 0 to 1000 μg/ml; (11) a concentrated stock of a washing solution to be diluted for use; (12) a pre-blocking solution for a pre-treatment of an antibody reaction including, for example, 0.1 to 10% skim milk, casein, bovine serum albumin, 4×SSC (a solution obtained by diluting 20×SSC: a mixture of 3 M sodium chloride and 0.3 M sodium citrate, pH 7.5), and 0 to 0.5% Triton X-100; (13) a detectable reporter system that can be reacted with a ligand or enzyme bound to RecA protein or an anti-RecA antibody; (14) an anti-fade solution for preventing fade of a fluorescent indicator obtained by, for example, dissolving 100 mg of p-phenylenediamine dihydrochloride in 10 ml of PBS, adding a 0.5 M carbonate-bicarbonate buffer of pH 9, thereto to attain pH 8 of the resultant mixture, further adding 90 ml of glycerol thereto and then filtering the resultant mixture with a filter of 0.22 μm. The kit can further include a counter stain such as propydium iodide (PI) and 4', 6-diamidino-2-phenylindol (DAPI).

In another aspect, the invention provides RecA protein with a label or ligand that can be used in the foregoing method. The RecA protein preferably includes a fluorescent indicator selected from the group consisting of fluoroscein isothiocyanate, carboxymethylindocyanine succinimidyl esters such as Cy3™ and Cy5™, rhodamine, Texas red (sulforhodamine), tetramethylrhodamine isothiocyanate and 7-amino-4-methylcoumarin-3-acetic acid at a proportion of 1 to 6 molecules per RecA protein monomer; an enzymatic label selected from the group consisting of alkaline phosphatase, peroxidase and β-galactosidase at a proportion of 1 to 3 molecules per RecA protein monomer; or a ligand selected from the group consisting of biotin and digoxigenin at a proportion of 1 to 6 molecules per RecA protein monomer.

In this manner, the present invention provides a diagnostically significant method by which the position of a specific gene or its regulatory region and the existence of a nucleic acid sequence derived from virus on a chromosome can be simply measured or visualized at high sensitivity without amplifying a signal.

According to the invention, a single copy gene, for example, a tumor suppressor gene such as p53 can be easily detected at high sensitivity. Furthermore, the present method is applicable to a CGH method (comparative genomic hybridization method) developed by Kallioniemi, A., et al. (Kallioniemi, A., et al., Science, 258, 818, 1992).

In the present method, any of the following genes and sequences can be a target: (1) a gene for encoding a specific useful gene product; (2) a gene having a significant cell regulatory function such as a ribosome gene, an oncogene and a tumor suppressor gene; (3) a repeated sequence and its related sequence; (4) a gene containing a genetic defect which prevents expression of an active gene product; (5) a gene or sequence related in chromosome position to a marker probe region with a known genetic map position; and (6) a viral gene sequence integrated into chromatin and a viral gene sequence in a viral particle, such as hepatitis B virus.

Furthermore, the present method can be used for detection of variation in ploidy of a chromosome, or various types of chromosomal aberration such as deletion, insertion, translocation, reversion, duplication and amplification. For example, through simultaneous hybridization reactions using a probe/RecA complex in which a complementary probe and RecA protein labeled with FITC are stably bound to a specific region, and another probe/RecA complex in which a complementary probe and RecA protein labeled with TRITC label are stably bound to another specific region, the respective regions can be detected with a fluorescence microscope at an appropriate excitation wavelength. Specifically, based on the positions of the two different identifiable fluorescent signals, the relative orientation of and distance between the two different genomic regions in the chromosome are determined, thereby detecting genetic aberration.

Alternatively, by the present method, changes in ploidy of a chromosome; various types of genetic aberration; and virus, bacteria, and parasitic pathogen in an organism, an organ, tissue and a cell, can be detected at high sensitivity. Thus, the method can be used for various diagnosis. The localization of nucleic acid of an infective virus or the like can be detected with a fluorescence microscope; or infected cells can be measured in a short period of time with an FACS (fluorescence activated cell sorter) or the like; so as to detect the level of infection, a percentage of the infected cells in sample cells, or the like. Therefore, for example, by measuring the decrease of the infected cells by the present method, the progress of a therapy using an antiviral agent can be evaluated.

In the present invention, since the hybridization reaction is performed by using a probe including neither a detectable label nor a detectable ligand under conditions where a target nucleic acid sequence is not denatured, the hybridization reaction is not disturbed by a label or ligand. Furthermore, since RecA protein including 1 to 6 molecules of a label or ligand per molecule of the protein can be bound to a probe at a proportion of approximately 3 bases per molecule; several to several hundreds times as much as the label or ligand can be added to the probe as compared with the case where the label or ligand is directly introduced into the probe. Therefore, it is possible to obtain a much stronger signal per target nucleic acid sequence than in the conventional method. In addition, since the bound RecA protein is detected, a target sequence with a smaller copy number can be detected at very high sensitivity and with high specificity.

EXAMPLES

Examples will now be described in order to describe the present invention. It is noted that these examples do not limit the invention but are merely exemplification thereof.

Example 1

Preparation of RecA Protein Including a Fluorescent Indicator

Commercially available RecA protein derived from E.coli (manufactured by Pharmacia) or RecA protein purified from ordinary E.coli by the method of Zarling, et al. (WO 93/05177) was used as RecA protein of this example. The molecular weight, the single-stranded DNA dependent ATPase activity, DNase activity, the strand transfer ability and the double D-loop forming ability of the employed RecA protein were previously measured by known methods (WO 93/05177; Sena, E. P. et al., Nature Genetics, 3, 365, 1993; Shibata. T., et al., Methods in Enzymology, 100, 197, 1983, etc.).

By using Fluorolink-Ab™ Cy3™ Labeling Kit or Fluorolink-Ab™ Cy5™ Labeling Kit, both manufactured by BIOLOGICAL DETECTION SYSTEMS, INC., Cy3™ or Cy5™ was bound to the RecA protein.

Specifically, 1 mg of the RecA protein dissolved in 1 ml of phosphate buffered saline (PBS), whose pH was adjusted to be 7.2, was poured into a vial containing 100 $\mu$l of a coupling buffer (1M sodium carbonate buffer, pH 9.3) and mixed. The resultant mixture was transferred to another vial containing Cy3™ or Cy5™ (the vial of reactive dye to label 1 mg of protein) to be mixed, and a reaction was performed at room temperature for 30 minutes. The thus obtained reaction solution was run on a gel filtration column included in the employed kit, and was eluted with an elution buffer (PBS, pH 7.2) included in the kit, thereby separating free Cy3™ or Cy5™ not having been bound to the RecA protein from a fraction including Cy3™ or Cy5™ bound to the RecA protein.

The thus obtained solution including the RecA protein bound to Cy3™ or Cy5™ was measured for the absorbance at wavelengths of 280 nm and 552 nm or 652 nm. Through the calculation based on the obtained absorbance A280 and A552 (in the case of Cy3™) or A652 (in the case of Cy5™), the RecA protein bound to Cy3™ or Cy5™ was found to include 1 to 2 molecules of $Cy_3$™ or Cy5™ per RecA protein monomer. (By varying the amount of the RecA protein to be used in the reaction between 0.3 and 2.0 mg per vial containing reactive dye to label 1 mg of protein, it is possible to prepare RecA protein including 1 to 6 molecules of Cy3™ or Cy5™ per RecA protein monomer, if necessary.)

FITC was bound to the RecA protein in the following manner: One ml of PBS including 1 mg of the RecA protein, whose pH was adjusted to be 7.2, was poured into a vial including 100 $\mu$l of a coupling buffer and mixed. The obtained mixture was transferred to another vial including 20 $\mu$g of FITC (1/50 of the RecA protein in weight) and mixed; a reaction was performed at room temperature for 20 minutes. The resultant reaction solution was run on a Sephadex G-25 column (manufactured by Pharmacia) and eluted with an elution buffer (PBS, pH 7.2), thereby separating free FITC not having been bound to the RecA protein from a fraction including the RecA protein bound to FITC. Through the calculation based on the absorbance A280 and A495, which were the absorbance of the solution including the RecA protein bound to FITC at wavelengths of 280 nm and 495 nm, the RecA protein bound to FITC was found to include 1 to 2 molecules of FITC per RecA protein monomer. (By varying the amount of FITC to be used in the reaction between 10 and 80 $\mu$g per 1 mg of the RecA protein, it is possible to prepare RecA protein including 1 to 6 molecules of FITC per RecA protein monomer, if necessary.)

TRITC was bound to the RecA protein in the similar manner to FITC. Specifically, 1 mg of the RecA protein was allowed to react with 40 μg of TRITC to obtain RecA protein including TRITC. The absorbance of the solution including the RecA protein bound to TRITC was similarly measured, to find that the RecA protein bound to TRITC included 1 to 2 molecules of TRITC per RecA protein monomer. (By varying the amount of TRITC used in the reaction between 20 and 200 μg per 1 mg of the RecA protein, it is possible to prepare RecA protein including 1 to 6 molecules of TRITC per RecA protein monomer, if necessary.)

Example 2

Preparation of an Anti-RecA Antibody Including a Fluorescent Indicator

An anti-RecA antibody was prepared by a known method such as one described in Seibutsukagaku Jikkenho 15 Menekigaku Jikken Nyumon published by Gakkai Shuppan Center. Specifically, antiserum including an anti-RecA antibody was obtained from mice that had received repeated injection of RecA protein into their abdominal cavities (100 to 200 μg of RecA per injection per mouse). The obtained antiserum was dialyzed against 0.01 M PBS, pH 7.2, overnight. The dialyzed antiserum was applied on a DEAE—cellulose column and eluted with 0.01 M PBS, pH 7.2, thereby obtaining a solution including the anti-RecA antibody (IgG fraction). The obtained solution including the anti-RecA antibody was concentrated to give a solution having an anti-RecA antibody concentration of at approximately 1 mg/ml. To the concentrated solution was added 1/10 volume of a coupling buffer. To the resultant solution was added a coupling buffer in which FITC with a weight 1/100 of that of the protein was dissolved, and a reaction was performed for 6 hours at a temperature of 7 to 9° C. The resultant reaction solution was run on a Sephadex G-25 column (manufactured by Pharmacia) and eluted with an elution buffer (0.01 M PBS, pH 7.2), thereby separating free FITC not having been bound to the anti-RecA antibody from a fraction including the anti-RecA antibody bound to FITC.

The obtained solution including the anti-RecA antibody bound to FITC was measured for the absorbance at the wavelengths of 280 nm and 495 nm. Through the calculation based on the measured absorbance A280 and A495, it was found that the anti-RecA antibody bound to FITC included 3 to 4 molecules of FITC per RecA protein monomer.

An anti-RecA antibody including TRITC was obtained similarly by using TRITC with a weight 1/40 of that of the anti-RecA antibody. This anti-RecA antibody was found to include 2 to 3 molecules of TRITC per RecA protein monomer.

Furthermore, in the same manner as in Example 1, Cy3™ or Cy5™ was bound to the anti-RecA antibody by using the Fluorolink-Ab™ Cy3™ Labeling Kit or the Fluorolink-Ab™ Cy5™ Labeling Kit, both manufactured by BIOLOGICAL DETECTION SYSTEMS, INC. One ml of a solution, including the anti-RecA antibody prepared having a concentration of 1 mg/ml as above, was used to find that the anti-RecA antibody bound to Cy3™ or Cy5™ included 4 to 5 molecules of Cy3™ or Cy5™ per RecA protein monomer.

Example 3

Detection of Chromosome #1 Satellite III Sequence by in situ Hybridization Using RecA Protein to which Cy3™ is bound (1) Preparation of a Hybridization Reaction Solution:

Plasmid pUC1.77 including a human chromosome #1 satellite III sequence (Cooke, H. J., et al., Nucleic Acids Res., 6, 3177, 1979) was labeled with biotin in the presence of bio-14-dATP (manufactured by Gibco-BRL) by using a nick translation kit manufactured by BRL, thereby preparing a biotinylated DNA probe including the chromosome #1 satellite III sequence. To the obtained biotinylated DNA probe solution was added a 1/10 volume of 3 M sodium acetate and subsequently a double volume of cooled ethanol, thereby precipitating the biotinylated DNA probe to be collected. Then, the collected probe was suspended in a Tris-hydrochloride EDTA buffer (10 mM Tris-hydrochrolide including 0.1 mM EDTA, pH 7.5).

The obtained suspended solution was diluted with sterilized water or a Tris-hydrochloride EDTA buffer, and the resultant solution was charged in a 0.6 ml microcentrifuge tube and heated for 5 minutes in boiling water, thereby denaturing the biotinylated DNA probe. The tube was transferred to ice water and rapidly cooled. Then, the solution including 50 ng of the thus denatured biotinylated DNA probe was poured into a 0.6 ml microcentrifuge tube including 1 μl of a 10×RecA reaction solution (20 mM magnesium acetate, 500 mM sodium acetate, 10 mM dithiothreitol, 1 mM EGTA (ethyleneglycol-bis(β-aminoethyl ether)N,N,N', N'-tetraacetic acid), and a 100 mM Tris-acetate buffer including 50% glycerol, pH 7.5), 1 μl of an ATPγS solution or of a GTPγS solution (at a concentration of 48.6 mM), 4 μg of RecA protein and 2 μg of RecA protein bound to Cy3™ obtained in Example 1. The resultant solution in the tube was diluted with sterilized water to attain a final volume of 10 μl, and a reaction was performed for 15 minutes at a temperature of 37° C.

Then, 1 μl of a solution including 40 μg/ml of salmon sperm DNA, obtained through denaturation similar to that of the biotinylated DNA probe, was added to the reaction solution and the reaction was further incubated for 10 minutes at a temperature of 37° C. To the resultant reaction solution was added 1 μl of a 100 mM magnesium acetate solution and homogeneously mixed, thereby giving a hybridization reaction solution.

(2) Preparation of HEp-2 Cell Nuclei:

HEp-2 cells (ATCC CCL23) derived from a human larynx epidermoid carcinoma were cultured by a general method in an MEM medium (manufactured by Gibco-BRL) including 10% bovine fetus serum, sodium pyruvate and antibiotics (penicillin, streptomycin). The obtained HEp-2 cells treated with trypsin-EDTA were collected by centrifugation at a low speed, and were gradually suspended in a 75 mM KCL solution in a water bath at a temperature of 37° C. While monitoring with a microscope, the cells were kept at this temperature for 5 to 20 minutes, thereby swelling the nuclei to an appropriate extent. Then, an ice cold methanol:acetic acid (3:1) mixture was added thereto, and the resultant mixture was centrifuged at a temperature of 0 to 4° C. Supernatant was removed, and an ice cold methanol:acetic acid (3:1) mixture was further added thereto, and the mixture was gently stirred and then centrifuged. This procedure was repeated approximately eight times, thereby removing cytoplasm and fixing the nuclei.

The obtained nuclei were resuspended in an ice cold methanol:acetic acid (3:1) mixture to give a suspended solution at a concentration of approximately 1 to $2 \times 10^6$ nuclei/ml. The obtained suspended solution was dropped on a slide glass by 10 μl aliquotes. The dropped suspended solution was dried with air, and then stored at a temperature ranging between room temperature and −80° C.

(3) A Hybridization Reaction with a Nondenatured Target Nucleic Acid Sequence and Detection of the Same:

To the sample including the target nucleic acid sequence on the slide glass prepared as described in (2) was added 100 μl of a protenase K solution at a concentration of 0.5 μg/ml (manufactured by Boehringer Mannheim, dissolved in PBS), and the resultant sample was covered with a PARAFILM® and treated for 3 minutes at a temperature of 37° C. After removing the proteinase K solution, the resultant sample was washed with PN (0.1 M phosphate buffered saline, pH 8.0, including 0.5% Nonidet P-40). Then, 100 μl of a pre-blocking solution (10 mM Tris-acetate buffer, pH 7.5, including 5% skim milk, 0.1% Triton X-100 and 0.02% sodium azide) was added to the sample, and the resultant sample was covered with a PARAFILM® and treated for 20 to 60 minutes at a temperature ranging from room temperature to 37° C., thereby blocking the sample. After removing the pre-blocking solution, the sample was lightly washed with 10 mM Trisacetate buffer, pH 7.5, and 10 μl of the hybridization reaction solution prepared in (1) was added thereto.

Then, the sample was covered with a coverslide, with care taken not to make a bubble therein, and the resultant was charged in a sealed container with humidity to perform a reaction in an incubator at a temperature of 37° C. for 2 hours. The thus obtained reaction sample was washed three times each for 10 minutes with 1.75×SSC (prepared by diluting 20×SSC: 3M sodium chloride and 0.3 M sodium citrate, pH 7.5). Then, the slide glass including the reaction sample was immersed in a blocking solution (4×SSC, 0.1% Triton X-100, 5% skim milk, 0.02% sodium azide) and incubated at room temperature for 20 minutes, thereby blocking the sample. Next, the sample was immersed in a blocking solution (4×SSC, 0.1% Triton X-100, 5% skim milk, 0.02% sodium azide) including 5 μg/ml of FITC avidin (manufactured by Vector, DCS grade, catalogue No: A-2011, lot No: C0527, F/P value: 4.6) and incubated at room temperature for 20 minutes. Thus, FITC avidin was allowed to bind to the biotinylated probe contained in the probe/RecA complex coupled to the target nucleic acid sequence. Then, the slide glass was washed successively with 4×SSC, 4×SSC including 0.1% Triton X-100 and 4×SSC in this order each for 10 minutes.

The slide glass was further washed lightly with sterilized water, and then to the sample was added a drop of an anti-fade solution (a solution obtained by dissolving 100 mg of p-phenylene diamine dihydrochloride in 10 ml of PBS, adding 0.5 M carbonate-bicarbonate buffer, pH 9, thereby attaining a final pH of 8, further adding 90 ml of glycerol and filtering the resultant solution with a 0.22 μm filter; to which a counter stain such as propydium iodide (PI) and 4', 6-diamidino-2-phenylindol (DAPI) can be added, if necessary), and the resultant glass slide was covered with a coverslide.

This sample was first observed with a fluorescence microscope manufactured by Olympus using a combination of a G excitation filter (BP-545) and an auxiliary excitation filter E0530 to detect a signal of Cy3™ derived from the RecA protein bound to Cy3™. Then, by using a combination of an IB excitation filter (BP-495) and an auxiliary absorbance filter (G520), a signal of FITC derived from the biotinylated probe contained in the complex of the target nucleic acid sequence and the probe. As a result, it was found that the signal of Cy3™ was stronger than that of FITC, and that the signal Cy3™ was positioned at exactly the same location as the signal of FITC. This revealed that the RecA protein remained in the obtained target nucleic acid/probe complex without being removed. It was also proved that the target nucleic acid/probe complex could efficiently formed within 2 hours by using RecA protein bound to Cy3™, and that by detecting the RecA protein bound to Cy3™ contained in the target nucleic acid/probe complex, the chromosome #1 satellite III sequence (the target nucleic acid sequence) could be detected without performing a staining procedure after the hybridization reaction and washing procedure, with higher sensitivity and with more ease and similar specificity as compared with the method by Zarling, et al. The usage of ATPγS or GTPγS as a cofactor made no difference in the result.

Example 4

Detection of a Chromosome #1 Satellite III Sequence by in situ Hybridization Using RecA Protein to which FITC is Bound (1) Preparation of a Hybridization Reaction Solution:

A DNA probe including a chromosome #1 satellite III sequence was prepared from plasmid pUC1.77 (Cooke, H. J., et al., Nucleic Acids Res., 6, 3177, 1979) including a chromosome #1 satellite sequence, in the presence of dNTP (dATP, dTTP, dGTP and dCTP) by using a nick translation kit manufactured by BRL. The obtained DNA probe did not include any label or ligand. To the obtained DNA probe solution was added a 1/10 volume of a 3M sodium acetate solution and successively a double volume of cooled ethanol to precipitate the DNA probe to be collected. The collected DNA probe was suspended in a 10 mM Tris-hydrochloride buffer, pH 7.5, including 0.1 mM EDTA.

The suspended solution was diluted with a Tris-hydrochloride buffer having the same composition or sterilized water, and the resultant solution was put in a 0.6 ml microcentrifuge tube and heated for 5 minutes in boiling water, thereby denaturing the probe. Then, the tube was transferred to ice water and rapidly cooled. A solution including 20 ng of the DNA probe denatured as above was poured into another 0.6 ml microcentrifuge tube including 1 μl of a 10×RecA reaction solution (100 mM Tris-acetate buffer, pH 7.5, including 20 mM magnesium acetate, 500 mM sodium acetate, 10 mM dithiothreitol, 1 mM EGTA and 50% glycerol), 1 μl of an ATPγS solution or GTPγS solution (stock with a concentration of 48.6 mM) (alternatively, rATP, dATP and a mixture of ATPγS with ADP), 1.6 μg of RecA protein and 0.8 μg of the RecA protein bound to FITC obtained in Example 1. The resultant solution was diluted with sterilized water to attain a final volume of 10 μl, and a reaction was performed for 15 minutes at a temperature of 37° C.

Then, to the resultant solution was added 1 μl of a salmon sperm DNA solution at a concentration of 40 μg/ml obtained through the similar denaturation to that of the DNA probe, and the reaction was further incubated for 10 minutes at a temperature of 37° C. One μl of a 100 mM magnesium acetate solution was added to the thus obtained reaction solution, and the resultant mixture was homogeneously mixed to give a hybridization reaction solution.

(2) Preparation of HEp-2 Cell Nuclei:

HEp-2 cell nuclei were prepared in the same manner as described in (2) of Example 3.

(3) A Hybridization Reaction with Nondenatured Target Nucleic Acid and Detection of the Same:

In the same manner as described in (3) of Example 3, a reaction was performed between the hybridization reaction solution prepared as described in (1) and the sample on a slide glass prepared as described in (2), and the resultant sample was washed successively with 1.75×SSC, 1.75×SSC including 0.1% Triton X-100 and 1.75×SSC each for 10 minutes at a temperature of 37° C. Then, the sample was lightly washed with sterilized water, and to the sample was added a drop of the anti-fade solution (including PI). A signal of FITC bound to the RecA protein included in the probe/RecA complex coupled to the target nucleic acid sequence was detected with a fluorescence microscope manufactured by Olympus using an IB excitation filter (BP-495).

The result of the observation demonstrated that, by using 20 ng of the probe and the RecA protein bound to FITC, the target nucleic acid/probe complex could be efficiently formed within 2 hours and that by detecting the RecA protein bound to FITC contained in the target nucleic acid/probe complex, the presence of the target nucleic acid sequence could easily be detected with an ordinary fluorescence microscope without performing a staining procedure after the hybridization reaction and washing procedure, even when the sample was counterstained. Thus, it was proven that the presence of a target nucleic acid sequence can be detected with higher sensitivity and more ease by the present method than by the method of Zarling, et al. The usage of ATPγS or GTPγS as a cofactor made no difference in the result.

Example 5

Detection of Tumor Suppressor Gene p53 by in situ Hybridization Using RecA Protein Including FITC (1) Preparation of a Hybridization Reaction Solution:

By using 20 ng of a biotinylated probe manufactured by ONCOR (manufactured by ONCOR, catalogue No: P1710-BIO, lot NO: 3C114) prepared from cDNA of tumor suppressor gene p53, a hybridization reaction solution was prepared in the same manner as described in (1) of Example 4.

(2) Preparation of HEp-2 Cell Nuclei:

HEp-2 cell nuclei were prepared in the same manner as described in (2) of Example 3.

(3) A Hybridization Reaction with Nondenatured Target Nucleic Acid and Detection of the Same:

A hybridization reaction with nondenatured target nucleic acid and detection thereof were performed in the same manner as described in (3) of Example 4. It was proven that, by using 20 ng of the p53 probe and the RecA protein bound to FITC, the target nucleic acid/probe complex could be efficiently formed within 2 hours, and that by detecting the RecA protein bound to FITC contained in the target nucleic acid/probe complex, the presence of the target nucleic acid sequence (herein the p53 gene sequence of single copy) could easily be detected with an ordinary fluorescence microscope without performing a staining procedure after the hybridization reaction and washing procedure, even when the sample was counterstained.

(4) Detection by the Method of Zarling, et al.:

Probe complexes were prepared in accordance with a method disclosed in Example 2 of WO 93/05177 by Zarling, et al., by using a combination of 50 ng of a biotinylated probe manufactured by ONCOR prepared from cDNA of p53 and 6 μg of RecA protein, and a combination of 20 ng of the biotinylated probe and 2.4 μg of RecA protein. Each complex was added to a sample prepared by the same manner as described in (2) of Example 3, and the resultant was subjected to hybridization in the same manner as described in Example 3B of WO 93/05177 by Zarling, et al., and then the resultant was washed. It is noted that the sample was pretreated before the hybridization, in a 10 mM Tris-acetate buffer (pH 7.5) for 45 minutes at a temperature of 60° C. A blocking treatment with a pre-blocking solution was not performed.

Next, by the method described in (3) of Example 3, FITC avidin (manufactured by Vector, DCS grade, catalogue No: A-2011, lot No: C0527, F/P value: 4.6) was allowed to bind to the biotinylated probe contained in the target nucleic acid/probe complex. The resultant was observed with a fluorescence microscope manufactured by Olympus by using an IB excitation filter (BP-495) to detect a signal of FITC derived from the biotinylated probe. When 50 ng of the biotinylated p53 probe was used, the signal was very weak but could be detected with the ordinary fluorescence microscope if the sample was not counterstained. When the sample was counterstained, the signal of FITC derived from the biotinylated p53 probe could not be detected.

When 20 ng of the biotinylated p53 probe was used, the signal of FITC derived from the biotinylated p53 probe could not be detected even if the sample was not counterstained. This result reveals that a p53 gene of single copy, can be detected with higher sensitivity and with more ease by the present method than by the method of Zarling, et al. The usage of ATPγS or GTPγS as a cofactor made no difference in the result.

Example 6

Detection of an HBV Nucleic Acid Sequence in a Suspended Solution Including Methanol Fixed Cells Derived from Hepatocellular Carcinoma by in situ Hybridization Using RecA Protein Including FITC (1) Preparation of a Hybridization Reaction Solution:

A plasmid pAM6 (ATCC 45020) including a total HBV (hepa-titis B virus) DNA sequence was fragmented in the presence of dNTP by using a nick translation kit manufactured by BRL, thereby preparing a DNA probe including the HBV sequence. The DNA probe did not include any detectable label or ligand. By using 20 ng of the thus prepared HBV probe, a hybridization reaction solution was prepared in the same manner as described in (1) of Example 4.

(2) Preparation of a Suspended Solution of Fixed Cells Derived from Hepatoma:

"Alexander" cells (ATCC CRL8024) derived from hepato-cellular carcinoma and known to include part of the HBV nucleic acid sequence in its chromosome were cultured in the same manner as the HEp-2 cells. The cultured cells were collected by centrifugation and washed with PBS. After removing the PBS by centrifugation, the precipitated cells were fixed by adding 100% ice cold methanol (or an appropriate fixing solution such as 70% ethanol). The cell concentration was adjusted to be $2\times10^6$ cells/ml, and the resultant solution was stored at a temperature of −20° C. A suspended solution of the HEp-2 cells was prepared as a control by fixing the cells in the same manner.

(3) A Hybridization Reaction with Nondenatured Target Nucleic Acid in the Cell Suspended Solution and Detection of the Same:

The cell suspension solution including approximately $1\times10^6$ cells prepared as described in (2) was charged in a 0.6 ml microcentrifuge tube and centrifuged at a temperature of 0 to 4° C., and supernatant was removed. The cells were air-dried, collected in the form of precipitation, and 200 μl of a pre-blocking solution was added thereto to suspend the cells. The suspended solution was allowed to stand for 20 to 30 minutes at a temperature ranging between room temperature and 37° C., thereby blocking the cells. The resultant solution was centrifuged to remove the pre-blocking solution, and the cells were washed with a 10 mM Tris-acetate buffer, pH 7.5. To the cells was added 10 μl of the hybridization reaction solution prepared as described in (1) to suspend the cells. A reaction was then performed in a water bath at a temperature of 37° C. for 2 hours.

The obtained reaction solution was centrifuged to remove the supernatant. Then, 200 μl of 1.75×SSC warmed at a temperature of 37° C. was added thereto to suspend the cells, and the resultant suspended solution was allowed to stand for 5 minutes in a water bath at a temperature of 37° C. The solution was then centrifuged to remove the supernatant. The resultant cells were further washed twice with 1.75× SSC including 0.1% Triton X-100 and 1.75×SSC in this order. Then, 30 μl of an anti-fade solution (excluding a counter stain such as PI) was added thereto to suspend the cells. Two μl of the resultant suspended solution was dropped on a slide glass, covered with a coverslide and observed for a signal of FITC with a fluorescence microscope manufactured by Olympus using an IB excitation filter (BP-495). As a result, a signal of FITC was detected in the Alexander cells without performing a staining procedure after the hybridization reaction and washing procedure, but no signal was detected in the HEp-2 cells.

This result proves that a target nucleic acid sequence can be detected with higher sensitivity and more ease by the present method even when a cell suspended solution is used. The usage of ATPγS or GTPγS. as a cofactor made no difference in the result.

Example 7

Detection of Chromosome #1 Satellite III DNA in a Chromosome Specimen Derived from Metaphase Cells by in situ Hybridization Using RecA Protein Including FITC (1) Preparation of a Hybridization Reaction Solution:

A hybridization reaction solution was prepared in the same manner as described in (1) of Example 4.

(2) Preparation of a Chromosomal Specimen:

A chromosome specimen was prepared by a general method such as one disclosed by Trask, B. J., et al., in Methods in Cell Biology, 35, 16, 1991, by culturing lymphocyte separated from healthy human blood, treating the cultured cells with colcemid and fixing the treated cells in the same manner as described in (2) of Example 3.

(3) A Hybridization Reaction with Nondenatured Target Nucleic Acid and Detection of the Same:

The same procedure as described in (3) of Example 4 was performed. It was proven that by using 20 ng of the probe and the RecA protein bound to FITC, the target nucleic acid and the target nucleic acid/probe complex in the chromosome specimen can be efficiently formed within 2 hours, and that by detecting FITC the presence of the chromosome #1 satellite III sequence, (the target nucleic acid sequence) in the chromosome specimen can easily be detected with an ordinary fluorescence microscope without performing a staining procedure after the hybridization reaction and washing procedure, even when the sample was counterstained. Thus, the present method was proven to be applicable to a chromosome specimen. The usage of ATPγS or GTPγS as a cofactor made no difference in the result.

Example 8

Detection of a Target Nucleic Acid Sequence (Chromosome #1 Satellite III Sequence) by Using an Anti-RecA Antibody Including FITC (1) Preparation of a Hybridization Reaction Solution:

By using 2.4 μg of RecA protein including no detectable label or ligand, a hybridization reaction solution was prepared in the same manner as described in (1) of Example 4.

(2) Preparation of HEp-2 Cell Nuclei:

HEp-2 cell nuclei were prepared in the same manner as described in (2) of Example 3.

(3) A Hybridization Reaction with Nondenatured Target Nucleic Acid and Detection of the Same:

To the sample prepared in (2) above was added 10 μl of the hybridization reaction solution prepared as described in (1). The reaction solution was covered with a coverslide with care taken not to make a bubble therein, and the slide glass was charged in a sealed container with humidity, and a reaction was performed in an incubator at a temperature of 37° C. for 2 hours. The resultant reaction sample was washed three times each for 10 minutes with 1.75×SSC warmed at a temperature of 37° C. Then, the slide glass including the sample was immersed in a blocking solution (4×SSC, 0.1% Triton X-100, 5% skim milk, 0.02% sodium azide) and incubated a reaction at room temperature for 20 minutes, thereby blocking the sample.

After removing the blocking solution, 100 μl of an anti-RecA antibody solution (a solution prepared by dissolving the anti-RecA antibody bound to FITC obtained in Example 2 in a blocking solution to attain a concentration of 15 μg/ml) was added thereto, and the resultant was covered with PARAFILD® to perform a reaction for 1 hour at a temperature of 37° C. The slide glass including the resultant sample was washed successively with 4×SSC, 4×SSC including 0.1% Triton X-100 and 4×SSC in this order each for 10 minutes at room temperature. The sample was further washed lightly with sterilized water, one drop of the anti-fade solution was added thereto and the resultant sample was covered with a coverslide. The sample was observed with a fluorescence microscope manufactured by Olympus using an IB excitation filter (BP-495), and the presence of the chromosome #1 satellite III DNA was detected by detecting a signal of FITC. The obtained signal was stronger than that obtained in Example 4. The usage of ATPγS or GTPγS as a cofactor made no difference in the result.

Example 9

Detection of a Target Nucleic Acid Sequence (Chromosome #1 Satellite III Sequence) by Using a Secondary Antibody that can Recognize an Anti-RecA Antibody (1) Preparation of a Hybridization Reaction Solution:

A hybridization reaction solution was prepared in the same manner as described in (1) of Example 8.

(2) Preparation of HEp-2 Cell Nuclei:

HEp-2 cell nuclei were prepared in the same manner as described in (2) of Example 3.

(3) A Hybridization Reaction with Nondenatured Target Nucleic Acid and Detection of the Same:

To the sample prepared in (2) above was added 10 μl of the hybridization reaction solution prepared in (1) above. The sample was covered with a coverslide with care taken not to make a bubble therein, and the resultant slide glass was performed in a sealed container with humidity, and a reaction was performed in an incubator at a temperature of 37° C. for 2 hours. The resultant reaction sample was washed three times each for 10 minutes with 1.75×SSC warmed at a temperature of 37° C. Next, the slide glass including the sample was immersed in a blocking solution (4×SSC, 0.1% Triton X-100, 5% skim milk, 0.02% sodium azide) and incubated at room temperature for 20 minutes, thereby blocking the cells. After removing the blocking solution, 100 μl of an anti-RecA antibody solution (a solution prepared by dissolving the anti-RecA antibody bound to FITC obtained in Example 2 in a blocking solution to attain a concentration of 15 μg/ml; an anti-RecA antibody not bound to FITC can be used) was added thereto, and the resultant sample was covered with a PARAFILM® to perform a reaction at a temperature of 37° C. for 1 hour. The slide glass including the sample was washed successively with 4×SSC, 4×SSC including 0.1% Triton X-100 and 4×SSC in this order each for 10 minutes at room temperature. The resultant slide glass was immersed in a blocking solution again and incubated at room temperature for 20 minutes, thereby blocking the cells again.

After removing the blocking solution, 100 μl of a goat anti-mouse IgG antibody solution (a solution prepared by 1/1000 diluting a goat anti-mouse IgG antibody manufactured by Sigma with PBS including 0.1% Tween-20 and 2% normal goat serum (manufactured by Gibco) ) was added thereto, and the resultant sample was covered with a PARAFILM®, and a reaction was performed at a temperature of 37° C. for 1 hour. The slide glass including the sample was washed with PBS including 0.1% Tween-20 at room temperature three times, each for 5 minutes. The slide glass was further washed lightly with sterilized water, a drop of the anti-fade solution was added thereto, and the resultant sample was covered with a coverslide. The sample was observed with a fluorescence microscope manufactured by Olympus using an IB excitation filter (BP-495), and the chromosome #1 satellite III DNA was detected by detecting a signal of FITC.

The obtained signal was much stronger than those obtained in Examples 4 and 8. The usage of ATPγS or GTPγS as a cofactor made no difference in the result.

Example 10

Detection of a Multiple Drug Resistance (MDR1) Gene by in situ Hybridization Using RecA Protein Including Digoxigenin (1) Preparation of RecA Protein Bound to Digoxigenin:

Digoxigenin was bound to RecA protein by using a DIG antibody labeling kit manufactured by Boehringer Mannheim.

Specifically, 1 mg of RecA protein was dissolved in 1 ml of a phosphate buffered saline (PBS), and to the resultant solution was added 43.5 μl of a digoxigenin-3-0-succinyl-ε-aminocaproic acid-N-hydroxy-succiimide ester (DIG-NHS) solution (2 μg/μl). A reaction was performed at room temperature for 2 hours with gently stirring. It is noted that 1 molar of the RecA protein reacts with 5 molars of DIG-NHS.

The obtained reaction solution was run on a Sephadex G-25 column, and eluted with an elution buffer (PBS, pH 7.2), thereby separating RecA bound to DIG-NHS from RecA protein not bound to DIG-NHS.

(2) Preparation of a Hybridization Reaction Solution:

A DNA probe including a cDNA sequence derived from a multiple drug resistance (MDR1) gene was prepared by using a nick translation kit manufactured by BRL in the presence of dNTP (dATP, dTTP, dGTP, dCTP) from a plasmid pMDRA1 including a cDNA sequence derived from the multiple drug resistance (MDR1) gene (Kioka, N., et al., Biochem. Biophys. Res. Commun., 162, 224, 1989). The obtained DNA probe included no detectable label or ligand. To a solution including the DNA probe was added ethanol including 0.3 M sodium acetate, thereby precipitating the DNA probe to be collected. The collected DNA probe was suspended in a Tris-hydrochrolide EDTA buffer (10 mM Tris-hydrochloride, 0.1 mM EDTA, pH 7.5) and purified with a Microcon-100 (manufactured by Amicon) to give a DNA probe solution.

The obtained DNA probe solution was diluted with sterilized water or a Tris-hydrochloride EDTA buffer and charged in a 0.6 ml microcentrifuge tube. The tube was kept in boiling water for 5 minutes, thereby denaturing the DNA probe. After the denaturation, the tube was moved into ice water and rapidly cooled.

In another 0.6 ml microcentrifuge tube, 1 μl of a 10×RecA reaction solution (100 mM Tris-acetate buffer, pH 7.5, 20 mM magnesium acetate, 500 mM sodium acetate, 10 mM dithiothreitol, 50% glycerol), 1 μl of an ATPγS or GTPγS solution (stock at a concentration of 4.86 mM), 114 ng of SSB (single-strand binding protein; manufactured by Pharmacia), 1.6 μg of RecA protein and 0.8 μg of RecA protein bound to DIG-NHS were mixed. The ATPγS or GTPγS solution was replaced with rATP, dATP or a mixture of ATPγS and ADP, when necessary.

To the microcentrifuge tube was added 20 ng of the DNA probe denatured as described above, and sterilized water was further added thereto to attain a final volume of 10 μl . Then, a reaction was performed at a temperature of 37° C. for 15 minutes.

One μl of a magnesium acetate solution (100 mM) was added to the resultant reaction solution and the mixture was homogeneously mixed to give a hybridization reaction solution.

(3) Preparation of HEp-2 Cell Nuclei:

HEp-2 cell nuclei were prepared in the same manner as described in (2) of Example 3.

(4) A Hybridization Reaction with Nondenatured Target Sequence and Detection of the Same:

To the HEp-2 cell nuclei on a slide glass obtained in (3) above was added 100 μl of an RNaseA solution (a solution prepared by dissolving RNaseA manufactured by Boehringer Mannheim in a 1×RecA reaction solution including no glycerol, to attain a final concentration of 50 μg/ml), and the resultant solution was covered with a PARAFILM® to be treated at a temperature of 37° C. for 60 minutes. After this treatment, the RNaseA solution was removed, and the sample was washed with a 1×RecA reaction solution including no glycerol. The resultant sample was treated with a 10% formalin solution (manufactured by Wako Pure Chemical Industries, Ltd.) at room temperature for 10 minutes.

Next, the sample was washed with a 1×RecA reaction solution including no glycerol, and 100 μl of a pre-blocking solution (5% skim milk, 10 mM Tris-acetate buffer, 0.1% Triton X-100, 0.02% sodium azide) was added thereto. The resultant sample was covered with a PARAFILM®, and allowed to stand for 20 to 60 minutes at a temperature ranging from room temperature to 37° C., thereby blocking the sample.

Then, the pre-blocking solution was removed, the sample was washed lightly with a 1×RecA reaction solution including no glycerol, and 10 μl of the hybridization reaction solution prepared in (2) above was added to the sample. The resultant sample was covered with a coverslide with care taken not to make a bubble therein, and the slide glass was charged in a sealed container with humidity, allowed to stand in an incubator at a temperature of 37° C. for 2 hours, thereby performing a hybridization reaction. The thus obtained reaction sample was washed with 1.75×SSC warmed to a temperature of 37° C. three times each for 10 minutes.

Then, the slide glass including the reaction sample was immersed in a blocking solution (4×SSC, 0.1% Triton X-100, 5% skim milk, 0.02% sodium azide) and incubated at room temperature for 20 minutes, thereby blocking the sample. Next, the slide glass including the sample was immersed in a blocking solution including 20 μg/ml of Anti-Digoxigenin-fluorescein, Fab fragment (manufactured by Boehringer Mannheim) and incubated at a temperature of 37° C. for 20 minutes, thereby allowing the Anti-Digoxigenin-fluorescein to bind to the RecA protein bound to DIG-NHS contained in the probe/RecA complex coupled to the target nucleic acid sequence. Then, the slide glass was washed successively with 4×SSC, 4×SSC including 0.1% Triton X-100 and 4×SSC in this order each for 10 minutes at room temperature. The slide glass was further washed lightly with sterilized water, and one drop of the anti-fade solution described referring to Example 3 was added thereto. The resultant sample was covered with a coverslide and observed with a fluorescence microscope manufactured by Olympus using an IB excitation filter (BP-495), thereby detecting a signal of fluorescein (FITC) derived from the RecA protein bound to DIG-NHS contained in the target nucleic acid (the cDNA sequence derived from the multiple drug resistance (MDR1) gene)/probe complex.

This result proves that a target nucleic acid/probe complex can be efficiently formed by using RecA protein bound to DIG-NHS, and that a single copy target sequence (herein a cDNA sequence derived from the multiple drug resistance (MDR1) gene) can be detected with higher sensitivity and more ease by detecting the RecA protein bound to DIG-NHS contained in the target nucleic acid/probe complex than by the method of Zarling, et al.

The usage of ATPγS or GTPγS as a cofactor made no difference in the result.

We claim:

1. A method for detecting the presence of a double-stranded target nucleic acid sequence contained in fixed cells or cell structures, the method comprising the steps of:
    obtaining the fixed cells or cell structures by fixing cells or cell structures so as to allow a nucleic acid probe to enter;
    forming a probe/labeled RecA complex in which a single-stranded probe and RecA protein having a detectable label or ligand are stably bound to each other, the single-stranded probe having a sequence complementary to the double-stranded target nucleic acid sequence;
    adding the probe/labeled RecA complex to the fixed cells or cell structures under conditions in which the probe/labeled RecA complex can come in contact with the double-stranded target nucleic acid sequence;
    allowing the probe/labeled RecA complex to react with the double-stranded target nucleic acid sequence so as to bind thereto under conditions where the double-stranded target nucleic acid sequence is not denatured;
    removing the unreacted part of the probe/labeled RecA complex that has not been bound to the double-stranded target nucleic acid sequence; and
    detecting the presence of the double-stranded target nucleic acid sequence by detecting the RecA protein having a detectable label or ligand included in the probe/labeled RecA complex bound to the double-stranded target nucleic acid.

2. A method according to claim 1, wherein the label or ligand is selected from the group consisting of a fluorescent indicator, a chemiluminescent agent, an enzymatic label, a radioactive label, biotin and digoxigenin.

3. A method according to claim 1, wherein the step of forming the probe/RecA complex is performed in the presence of a cofactor selected from the group consisting of ATPγS, GTPγS, rATP, DATP, a mixture of ATPγS and rATP, and a mixture of ATPγS and ADP.

4. A method according to claim 2, wherein the fluorescent indicator is selected from the group consisting of fluoroscein isothiocyanate, carboxymethylindocyanine succinimidyl ester, rhodamine, Texas red (sulforhodamine), tetramethylrhodamine isothiocyanate, and 7-amino-4-methylcoumarin-3-acetic acid.

5. A method according to claim 1, wherein the label is a fluorescent indicator, and the step of detecting the presence of the double-stranded target nucleic acid sequence is performed with a fluorescence microscope or a flow cytometer.

6. A method according to claim 2, wherein the enzymatic label is selected from the group consisting of alkaline phosphatase, peroxidase and β-galactosidase.

7. A method according to claim 1, wherein the step of detecting the presence of the double-stranded target nucleic acid sequence is performed by further using an anti-RecA antibody.

8. A method according to claim 7, wherein the anti-RecA antibody has a detectable label or ligand.

9. A method according to claim 8, wherein the label or ligand is selected from the group consisting of a fluorescent indicator, a chemiluminescent agent, an enzymatic label, a radioactive label, biotin and digoxigenin.

10. A method according to claim 9, wherein the fluorescent indicator is selected from the group consisting of fluoroscein isothiocyanate, carboxymethylindocyanine succinimidyl ester, rhodamine, Texas red (sulforhodamine), tetramethylrhodamine isothiocyanate, and 7-amino-4-methylcoumarin-3-acetic acid.

11. A method according to claim 9, wherein the label is a fluorescent indicator, and the step of detecting the presence of the double-stranded target nucleic acid sequence is performed with a fluorescence microscope or a flow cytometer.

12. A method according to claim 9, wherein the enzymatic label is selected from the group consisting of alkaline phosphatase, peroxidase and β-galactosidase.

13. A method according to claim 1, wherein the step of detecting the presence of the double-stranded target nucleic acid sequence is performed by further using an anti-RecA antibody and a secondary antibody having a detectable label or ligand that can bind to an anti-RecA antibody.

14. A kit including RecA protein having a detectable label or ligand, for use in practicing a method for detecting the presence of a double-stranded target nucleic acid sequence contained in fixed cells or cell structures, the method comprising the steps of:

obtaining the fixed cells or cell structures by fixing cells or cell structures so as to allow a nucleic acid probe to enter;

forming a probe/labeled RecA complex in which a single stranded probe and RecA protein having a detectable label or ligand are stably bound to each other, the single-stranded probe having a sequence complementary to the double-stranded target nucleic acid sequence;

adding the probe/labeled RecA complex to the fixed cells or cell structures under conditions in which the probe/labeled RecA complex can come in contact with the double-stranded target nucleic acid sequence;

allowing the probe/labeled RecA complex to react with the double-stranded target nucleic acid sequence so as to bind thereto under conditions where the double-stranded target nucleic acid sequence is not denatured;

removing the unreacted part of the probe/labeled RecA complex that has not been bound to the double-stranded target nucleic acid sequence; and detecting the presence of the double-stranded target nucleic acid sequence by detecting the RecA protein having a detectable label or ligand included in the probe/labeled RecA complex bound to the double-stranded target nucleic acid.

15. A kit according to claim 14, wherein the label or ligand is selected from the group consisting of a fluorescent indicator, a chemiluminescent agent, an enzymatic label, a radioactive label, biotin and digoxigenin.

16. A kit according to claim 15, wherein the fluorescent indicator is selected from the group consisting of fluoroscein isothiocyanate, carboxymethylindocyanine succinimidyl ester, rhodamine, Texas red (sulforhodamine), tetramethylrhodamine isothiocyanate, and 7-amino-4-methylcoumarin-3-acetic acid.

17. A kit according to claim 15, wherein the enzymatic label is selected from the group consisting of alkaline phosphatase, peroxidase and β-galactosidase.

18. A kit including probe/labeled RecA complex in which a probe and RecA protein having a detectable label or ligand are stably bound to each other, for use in practicing a method for detecting the presence of a double-stranded target nucleic acid sequence contained in fixed cells or cell structures, the method comprising the steps of:

obtaining the fixed cells or cell structures by fixing cells or cell structures so as to allow a nucleic acid probe to enter;

forming a probe/labeled RecA complex in which a single-stranded probe and RecA protein having a detectable label or ligand are stably bound to each other, the single-stranded probe having a sequence complementary to the double-stranded target nucleic acid sequence, adding the probe/labeled RecA complex to the fixed cells or cell structures under conditions in which the probe/labeled RecA complex can come in contact with the double stranded target nucleic acid sequence;

allowing the probe/labeled RecA complex to react with the double-stranded target nucleic acid sequence so as to bind thereto under conditions where the double-stranded target nucleic acid sequence is not denatured;

removing the unreacted part of the probe/labeled RecA complex that has not been bound to the double-stranded target nucleic acid sequence; and detecting the presence of the double-stranded target nucleic acid sequence by detecting the RecA protein having a detectable label or ligand included in the probe/labeled RecA complex bound to the double-stranded target nucleic acid.

19. A kit according to claim 18, wherein the label or ligand is selected from the group consisting of a fluorescent indicator, a chemiluminescent agent, an enzymatic label, a radioactive label, biotin and digoxigenin.

20. A kit according to claim 19, wherein the fluorescent indicator is selected from the group consisting of fluoroscein isothiocyanate, carboxymethylindocyanine succinimidyl ester, rhodamine, Texas red (sulforhodamine), tetramethylrhodamine isothiocyanate, and 7-amino-4-methylcoumarin-3-acetic acid.

21. A kit according to claim 19, wherein the enzymatic label is selected from the group consisting of alkaline phosphatase, peroxidase and β-galactosidase.

22. A kit including RecA protein and an anti-RecA antibody comprising:

RecA protein and an anti-RecA antibody both having a detectable label or ligand, wherein the kit is used for practicing a method for detecting the presence of a double-stranded target nucleic acid sequence contained in fixed cells or cell structures, the method comprising the steps of:

obtaining the fixed cells or cell structures by fixing cells or cell structures so as to allow a nucleic acid probe to enter;

forming a probe/labeled RecA complex in which a single-stranded probe and RecA protein having a detectable label or ligand are stably bound to each other, the single-stranded probe having a sequence complementary to the double-stranded target nucleic acid sequence;

adding the probe/labeled RecA complex to the fixed cells or cell structures under conditions in which the probe/labeled RecA complex can come in contact with the double-stranded target nucleic acid sequence;

allowing the probe/labeled RecA complex to react with the double-stranded target nucleic acid sequence so as to bind thereto under conditions where the double-stranded target nucleic acid sequence is not denatured;

removing the unreacted part of the probe/labeled RecA complex that has not been bound to the double-stranded target nucleic acid sequence; and detecting the presence of the double-stranded target nucleic acid sequence by detecting the RecA protein having a detectable label or ligand included in the probe/labeled RecA complex bound to the double-stranded target nucleic acid, wherein the step of detecting the presence of the double-stranded target nucleic acid sequence is performed by further using an anti-RecA antibody having a detectable label or ligand.

23. A kit according to claim 22, wherein the label or ligand is selected from the group consisting of a fluorescent indicator, a chemiluminescent agent, an enzymatic label, a radioactive label , biotin and digoxigenin.

24. A kit according to claim 23,
wherein the fluorescent indicator is selected from the group consisting of fluoroscein isothiocyanate, carboxymethylindocyanine succinimidyl ester, rhodamine, Texas red (sulforhodamine), tetramethylrhodamine isothiocyanate, and 7-amino-4-methylcoumarin-3-acetic acid.

25. A kit according to claim 23,
wherein the enzymatic label is selected from the group consisting of alkaline phosphatase, peroxidase and β-galactosidase.

26. A kit including a probe/labeled RecA complex comprising:
RecA protein and an anti-RecA antibody both having a detectable label or ligand,
wherein the RecA protein, having the detectable label or ligand, and a probe are stably bound to each other, for use in practicing a method for detecting the presence of a double-stranded target nucleic acid sequence contained in fixed cells or cell structures, the method comprising the steps of:
obtaining the fixed cells or cell structures by fixing cells or cell structures so as to allow a nucleic acid probe to enter;
forming a probe/labeled RecA complex in which a single-stranded probe and RecA protein having a detectable label or ligand are stably bound to each other, the single-stranded probe having a sequence complementary to the double-stranded target nucleic acid sequence;
adding the probe/labeled RecA complex to the fixed cells or cell structures under conditions in which the probe/labeled RecA complex can come in contact with the double-stranded target nucleic acid sequence;
allowing the probe/labeled RecA complex to react with the double-stranded target nucleic acid sequence so as to bind thereto under conditions where the double-stranded target nucleic acid sequence is not denatured;
removing the unreacted part of the probe/labeled RecA complex that has not been bound to the double-stranded target nucleic acid sequence; and
detecting the presence of the double-stranded target nucleic acid sequence by detecting the RecA protein having a detectable label or ligand included in the probe/labeled RecA complex bound to the double-stranded target nucleic acid,
wherein the step of detecting the presence of the double-stranded target nucleic acid sequence is performed by further using anti-RecA antibody having a detectable label or ligand.

27. A kit according to claim 26,
wherein the label or ligand is selected from the group consisting of a fluorescent indicator, a chemiluminescent agent, an enzymatic label, a radioactive label, biotin and digoxigenin.

28. A kit according to claim 27,
wherein the fluorescent indicator is selected from the group consisting of fluoroscein isothiocyanate, carboxymethylindocyanine succinimidyl ester, rhodamine, Texas red (sulforhodamine), tetramethylrhodamine isothiocyanate, and 7-amino-4-methylcoumarin-3-acetic acid.

29. A kit according to claim 27,
wherein the enzymatic label is selected from the group consisting of alkaline phosphatase, peroxidase and β-galactosidase.

30. RecA protein
having a label or ligand selected from the group consisting of an enzymatic label, biotin and digoxigenin.

31. RecA protein according to claim 30 comprising, per RecA protein monomer, 1 to 3 molecules of an enzymatic label selected from the group consisting of alkaline phosphatase, peroxidase and β-galactosidase.

32. RecA protein according to claim 30 comprising, per RecA protein monomer, 1 to 6 molecules of a ligand selected from the group consisting of biotin and digoxigenin.

33. A method according to claim 1, further comprising a step of treating the fixed cells or cell structures with a pre-blocking solution in order to prevent the non-specific binding of the RecA protein having a detectable label or ligand to a component in the fixed cells or cell structures.

34. A method according to claim 33,
wherein the pre-blocking solution includes at least one selected from the group consisting of casein, skim milk, bovine serum albumin, carrier DNA and carrier RNA that is hybridized with neither nucleic acid contained in the cells or cell structures nor the probe.

* * * * *